United States Patent [19]

Tarrson et al.

[11] 4,319,377
[45] Mar. 16, 1982

[54] INTERPROXIMAL TOOTHBRUSH

[75] Inventors: Emanuel B. Tarrson; Dane Maric, both of Chicago, Ill.

[73] Assignee: John O. Butler Company, Chicago, Ill.

[21] Appl. No.: 180,812

[22] Filed: Aug. 25, 1980

[51] Int. Cl.³ .......................... A46B 3/08; A46B 3/18; A46B 9/04
[52] U.S. Cl. .......................................... 15/111; 15/145; 15/167 R; 15/176; 132/89
[58] Field of Search .................. 15/105, 110, 111, 172, 15/176, 206, 167 R, 145; D24/11; 132/89

[56] References Cited

U.S. PATENT DOCUMENTS

| | | | |
|---|---|---|---|
| 1,173,721 | 2/1916 | Hurvitz | 15/206 X |
| 1,996,205 | 4/1935 | Jackson | 15/167 R X |
| 3,204,275 | 9/1965 | Baker | 15/172 |
| 3,559,226 | 2/1971 | Burns | 15/206 X |
| 4,222,143 | 9/1980 | Tarrson et al. | 15/105 |

FOREIGN PATENT DOCUMENTS 544870  4/1942  United Kingdom ............ 15/206

Primary Examiner—Peter Feldman
Attorney, Agent, or Firm—Laff, Whitesel, Conte & Saret

[57] ABSTRACT

An interproximal toothbrush comprises an elongated metal handle terminating at one end in a threaded section. The stem of a twisted wire brush passes through a hole in said threaded section, humps up above the threads, and then passes down into a groove in the handle. A nut travels on the threads until it encounters and seizes upon the hump in the twisted wire. This way, the brush is securely locked into position, but the nut never touches the stem in the area of the brush. Thus, the brush is not damaged by the locking nut. A second hole in the handle receives a toothpick.

7 Claims, 6 Drawing Figures

INTERPROXIMAL TOOTHBRUSH

This invention relates to brushes and brush handles and, more particularly, to interproximal toothbrushes for cleaning the spaces between and around human teeth.

Reference is made to U.S. Pat. No. 3,559,226 (R. L. Burns, inventor), and to co-pending applications Ser. No. 21,116, now U.S. Pat. No. 4,222,143, filed Mar. 16, 1979; Ser. No. 17,826, now U.S. Pat. No. D. 262,236 filed Mar. 5, 1979; and Ser. No. 290, now U.S. Pat. No. D. 262,315, and Ser. No. 291, now U.S. Pat. No. D. 262,316, both filed Dec. 28, 1978, which show other interproximal brushes and handles. The present invention is an improvement over the structures seen in this patent and these applications.

In general, an interproximal brush is an item which wears out quickly and, therefore, should preferably be easily replaceable in its handle. The brush projects more or less perpendicularly away from its handle in order to brush within the spaces between the teeth, under and around bridges, and the like. Thus, its handle must include some kind of a chuck which provides a sturdy and reliable support for the brush stem.

This form of support creates two problems. First, there is a problem of insuring a secure anchorage so that the brush can not fall out of the handle during use. Second, there may be a material fatigue which occurs within the stem of a twisted wire brush when the brush wiggles back and forth in the handle, as brushing occurs.

In order to easily replace the brush, the handle and the brush chuck must also be fairly simple and easy to use. The above-cited U.S. Pat. No. 3,559,226 shows a metal brush handle having a diametric hole for receiving the stem of a twisted wire brush. A nut is threaded onto the handle and run up the handle to a point which is inboard of the hole. The brush stem is inserted through the hole and then the nut is turned to engage the stem of a twisted wire brush. Many people turn the nut so forcefully that they nick the twisted wire so that it breaks off when the brush bends back and forth while in use. Sometimes, they even turn the nut so forcefully that they completely ruin the brush, breaking it or straightening it to project in alignment with the handle.

The co-pending applications show an interproximal brush handle which eliminates the metal handle and nut in favor of a plastic combination of a handle and a sleeve, which bound the twisted wire brush stem to the handle.

In addition, other tooth care problems should be performed at about the same time as the interproximal brushing, such as cleaning between the teeth with a toothpick. Therefore, it is convenient if the handle also includes means for holding a toothpick.

Accordingly, an object of the invention is to provide an interproximal brush having a metal handle which prevents a damaging of the stem of a twisted wire brush.

Another object of the invention is to provide a foolproof interproximal handle structure which is easy to use.

In keeping with an aspect of the invention, these and other objects are accomplished by an elongated metal handle having an angular, threaded end which is diametrically pierced by a pair of holes lying in the plane of the angle. A radiused, longitudinal groove extends from a first of these holes, back along the length of the handle. When turned, a threaded nut travels over the length of the groove and advances toward the first hole. The stem of a twisted wire brush passes through the first hole, bends and lies in the groove in such a manner that it must hump up in order to form an obstruction to limit the forward excursion of the nut. The hump of the twisted wire functions both as a locking device for stopping the forward travel of the nut and as an anchor point for securing the twisted wire brush. The second hole receives a toothpick and also provides a means for pushing the twisted wire stem out of the groove, if it should become necessary to do so. The second hole terminates within the groove so that any splintered ends are below the surface.

A preferred embodiment of the invention is seen in the attached drawing, wherein.

The handle 10 is an elongated bar with a bent portion terminating in a threaded end 12. The opposite end of the handle is knurled at 14 to facilitate holding it with wet hands. At 16, the elongated handle is bent at an angle a (FIG. 2) of about 15° to 25°, which offsets the brush end in a manner that makes it easy to brush in and around the teeth.

Figure 1:
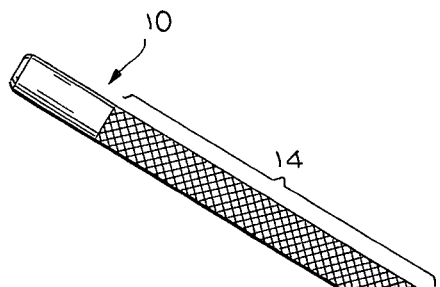
FIG. 1 is a side elevation of the brush handle with an interproximal brush locked therein.
Figure 2:
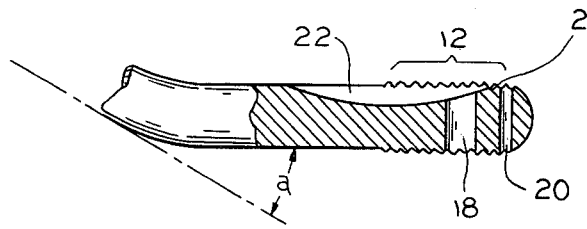
FIG. 2 is a cross-sectional view of a fragment of the end of the handle, taken along line 2—2 of FIG. 1.

In the plane of the bend 16, the threaded end 12 of the handle 10 is pierced by two diagonal holes, best seen in FIG. 2. A first of these holes, 20, is near the end of the handle and has a relatively small diameter. The second of these holes 18 is inboard from the first, and has a relatively large diameter.

A slot or groove 22 extends longitudinally away from the first hole 20 and up the length of the handle. This groove 22 begins at a relatively high shoulder 23, near hole 20, and then curves downwardly with a radius. Conveniently, this groove may be formed on a punch press, which leaves serrations in the bottom of the groove. It can also be cut by a circular saw blade which is lowered into the handle. The threaded portion 12 extends across both holes and the groove 22. A knurled, threaded nut 24 fits onto the threads.

Figure 3:
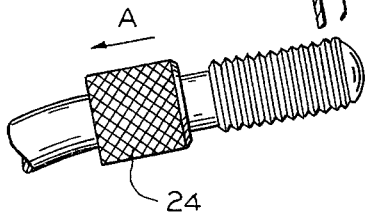
FIG. 3 is a first stop-motion view showing the insertion of the stem of twisted wire brush into the handle.

The twisted wire brush 26 has a stem portion 28 (FIG. 3) which slides easily (but without too much clearance) through the hole 20 and then bends over to be pressed into the groove 22.

Figure 4:
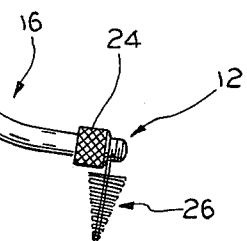
FIG. 4 is a second stop-motion view showing the next and stem-bending step in the insertion of a twisted wire brush.
Figure 5:
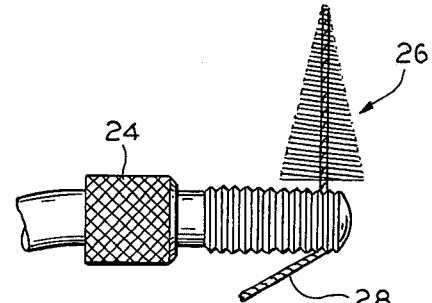
FIG. 5 is a third stop-motion view (partially in cross section) showing the twisted wire brush locked in position.
Figure 6:
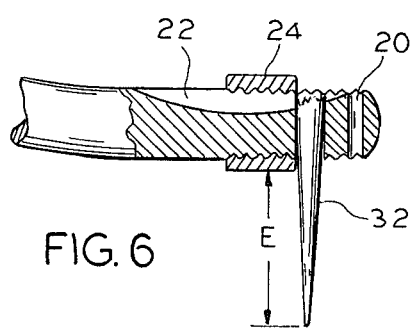
FIG. 6 is a fragment of the end of FIG. 1 which shows the handle being used to hold an end of a toothpick.

In order to load a brush (FIG. 3) into the handle, the nut 24 is first turned so that it moves (direction A) away from the threaded end 12 to expose the groove 22 and holes 20, 18. Then, the stem 28 of the brush 26 is passed (direction B) into the hole 20. The stem 28 is bent (FIG. 4) over and pressed into the groove 22. As it bends over shoulder 23, stem 28 forms a hump 30 (FIG. 5), which projects above the threads 12.

The nut 24 (FIG. 5) is turned on threads 12 to advance (direction C) toward the hump 30. As it does so advance, the stem 28 of the twisted wire brush is pressed down and into the groove 22. The nut passes over the pressed-down stem and comes into contact with the hump 30, where it tends to take a bite upon the hump 30 and to lock itself into position.

It should be carefully noted that at the point where nut 24 jams against the hump 30, and cannot travel any further, there is still a distance D separating the nut from the stem 28. Therefore, there is no way for the nut to nick or bend the wire stem. Thus, even the most enthusiastic user cannot advance the nut far enough to damage the brush.

Also, the brush is securely held in place. The diameter of hole 20 is small enough and the hole is long enough to prevent any substantial amount of metal fatiguing, lateral movement of the twisted wire stem. In the hump 30 area, the threads of the nut tend to press against and to bite into the metal of the twisted wire stem 28 while anchoring it against the bottom of the groove 22.

In order to use a toothpick, the nut 24 is backed off (in direction A). Then, a round toothpick 32 is pushed firmly into the hole 18, tightly enough to wedge it into position. The diameter of hole 18 is related to the diameter of a wooden toothpick so that it projects a predetermined distance E though the hole, when wedged in place. Then, the toothpick is snapped off above the hole 18. Any splintered end of the toothpick is contained within the groove 22 so that it will not scratch the user. The nut 24 may be run up against the wood to hold it in place.

The advantages of the invention are that it gives the quality and sales appeal of a metal handle, without damage to the twisted wire stem. It prevents inadvertent movement of the nut too far toward the end of the brush.

Those who are skilled in the art will readily perceive how to modify the system. Therefore, the appended claims are to be construed to cover all equivalent structures which fall within the true scope and spirit of the invention.

I claim:

1. An interproximal brush handle comprising an elongated handle part having a bend near one end, said handle terminating in a threaded portion at the bent end, at least one hole lying in the plane of said bend and extending diametrically through said threaded portion of said handle, said hole having a diameter which receives a twisted wire brush stem, a groove having a lower surface beginning near the top of said hole at a point which is displaced downwardly into said handle by a distance which is less than the thickness of said twisted wire brush stem, said groove further extending downwardly along the length of said handle to a depth which is more than the thickness of said twisted wire, and a nut turned on said threaded portion, the lower surface of the groove near the top of the hole being high enough so that a twisted wire brush stem extending through said hole and pressed down into said groove forms a hump projecting above the threads far enough to terminate the forward motion of said nut as it travels toward the end of said handle.

2. The handle of claim 1 wherein said hole has a diameter which enables said twisted wire to pass easily, but snugly therethrough.

3. The handle of claim 1 or claim 2 and a second hole lying in the plane of said bend and extending diametrically through said threaded portion, said second hole having a diameter which receives a predetermined length of a wooden toothpick, when wedged therein.

4. The handle of claim 1 or claim 2 wherein said groove is formed with a radius in the plane of said bend.

5. The handle of claim 3 wherein said second hole is positioned relative to the groove and to said first hole so that the second hole receives a tool for pushing the twisted stem out of the groove.

6. The handle of claim 3 wherein said hole terminates within said groove so that any splinters on said toothpick are within said groove.

7. An interproximal toothbrush comprising a metal handle and a twisted wire brush having a stem of a predetermined thickness formed by said twisted wire, said handle comprising an elongated metal bar terminated at one end in a threaded section, at least one hole piercing said threaded section, said hole having a diameter which easily but somewhat snugly enables said stem to pass therethrough, a stem receiving groove beginning a distance which is less than the predetermined thickness below the top of said hole and extending downwardly into said handle and longitudinally along the length of said handle in a direction which is away from the threaded end, said groove ending at a depth in said handle which is greater than said predetermined thickness, whereby said groove has dimensions such that said wire stem forms a hump which projects above said threads and then fits down into said groove, and a nut on said threads which passes over a stem in said groove to engage and secure the hump of said wire stem.

* * * * *